US011051512B2

(12) United States Patent
Olson et al.

(10) Patent No.: US 11,051,512 B2
(45) Date of Patent: *Jul. 6, 2021

(54) TRIAMINE SOLIDIFICATION USING DIACIDS

(71) Applicant: Ecolab USA Inc., Saint Paul, MN (US)

(72) Inventors: Erik C. Olson, Saint Paul, MN (US); Carter M. Silvernail, Saint Paul, MN (US); Gregory G. Griese, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/574,431

(22) Filed: Sep. 18, 2019

(65) Prior Publication Data
US 2020/0008423 A1 Jan. 9, 2020

Related U.S. Application Data

(63) Continuation of application No. 15/267,363, filed on Sep. 16, 2016, now Pat. No. 10,463,041.
(Continued)

(51) Int. Cl.
A01N 33/04 (2006.01)
C11D 17/00 (2006.01)
C10M 105/30 (2006.01)
C11D 7/32 (2006.01)
C11D 7/26 (2006.01)
C10M 105/00 (2006.01)
C10M 105/26 (2006.01)
C07C 209/68 (2006.01)
C07C 211/14 (2006.01)
A01N 25/12 (2006.01)
A01N 25/30 (2006.01)
A61L 2/23 (2006.01)
C10M 141/06 (2006.01)
C11D 3/20 (2006.01)
C11D 3/30 (2006.01)
C11D 3/386 (2006.01)
(Continued)

(52) U.S. Cl.
CPC ............. A01N 33/04 (2013.01); A01N 25/12 (2013.01); A01N 25/30 (2013.01); A61L 2/23 (2013.01); C07C 209/68 (2013.01); C07C 211/14 (2013.01); C10M 105/00 (2013.01); C10M 105/26 (2013.01); C10M 105/30 (2013.01); C10M 141/06 (2013.01); C11D 3/2082 (2013.01); C11D 3/2086 (2013.01); C11D 3/30 (2013.01); C11D 3/38627 (2013.01); C11D 3/48 (2013.01); C11D 7/265 (2013.01); C11D 7/3209 (2013.01); C11D 17/0047 (2013.01); C11D 17/0052 (2013.01); C10M 2207/123 (2013.01); C10M 2207/124 (2013.01); C10M 2207/127 (2013.01); C10M 2207/1233 (2013.01); C10M 2207/1273 (2013.01); C10M 2207/142 (2013.01); C10M 2207/144 (2013.01); C10M 2207/1423 (2013.01); C10M 2207/1443 (2013.01); C10M 2215/04 (2013.01); C10M 2215/041 (2013.01); C10N 2050/08 (2013.01); C12Y 301/01 (2013.01)

(58) Field of Classification Search
CPC .............. C10M 105/00; C10M 105/26; C10M 141/06; C10M 105/30; C10M 2207/123; C10M 2207/1233; C10M 2207/1443; C10M 2207/1273; C10M 2207/144; C10M 2207/142; C10M 2207/124; C10M 2215/04; C10M 2207/1423; C10M 2207/127; C10M 2215/041; C11D 17/0047; C11D 3/48; C11D 3/2086; C11D 7/265; C11D 7/3209; A61L 2/23; A01N 25/30; A01N 25/12; A01N 33/04; C07C 209/68; C07C 211/14; C12Y 301/01; C10N 2050/08
See application file for complete search history.

(56) References Cited

U.S. PATENT DOCUMENTS 2,982,665 A 5/1961 Wilcox
7,727,949 B2 6/2010 Manabe et al.
(Continued)

FOREIGN PATENT DOCUMENTS

AU 2004239072 B2 11/2004
AU 2005296748 B2 4/2006
(Continued)

OTHER PUBLICATIONS

MSDS for Acetic acid from Sigma-Aldrich citing the Merck Index, 12th ed., #52 (1996).*
Galego, N. et al., "Citric-Acid-Diethylenetriamine Salts as Latent Curing Agents for Epoxy Resins", Journal of Applied Polymer Science, vol. 45, pp. 607-610, 1992.
Hofmann, A.W., "Notes of Researches on the Poly-Ammonias, No. XVI. Triatomic Ammonias", Proceedings of the Royal Society of London, vol. 11, pp. 413-419, 1860.
Ecolab USA Inc., PCT/US2016/052141 filed Sep. 16, 2016, "The International Search Report and the Written Opinion of the International Searching Authority, or the Declaration and the Written Opinion of the International Searching Authority", 13 pages, dated Dec. 25, 2016.
(Continued)

Primary Examiner — Blessing M Fubara
(74) Attorney, Agent, or Firm — McKee, Voorhees & Sease, PLC

(57) ABSTRACT

Stable, solid triamine compositions are disclosed. The pressed, cast, extruded or other solid compositions are suitable for antimicrobial, sanitizing and disinfectant applications. Ready-to-use solutions are obtained by dissolving the solid triamine compositions with water and the methods of use thereof are particularly suitable for cleaning, disinfecting, sanitizing, rinsing and/or lubricating. Beneficially, the solid triamine compositions are at least partially neutralized, allowing activity of 90% and greater of the biocidal triamine, and provide at least substantially similar or superior performance and micro efficacy to liquid formulations.

20 Claims, No Drawings

Related U.S. Application Data

(60) Provisional application No. 62/219,781, filed on Sep. 17, 2015.

(51) Int. Cl.
*C11D 3/48* (2006.01)
*C10N 50/08* (2006.01)

(56) References Cited

U.S. PATENT DOCUMENTS

| | | |
|---|---|---|
| 7,795,199 B2 | 9/2010 | Molinaro et al. |
| 7,851,420 B2 | 12/2010 | Theunissen et al. |
| 7,951,767 B2 | 5/2011 | Molinaro et al. |
| 8,118,968 B2 | 2/2012 | Moeller et al. |
| 8,211,733 B2 | 7/2012 | Sato et al. |
| 8,211,849 B2 | 7/2012 | Molinaro et al. |
| 8,221,733 B2 | 7/2012 | Lichtenberg et al. |
| 8,524,807 B2 | 9/2013 | Butikofer |
| 8,569,373 B2 | 10/2013 | Foret et al. |
| 2009/0093443 A1 | 4/2009 | Kempen et al. |
| 2009/0102085 A1 | 4/2009 | Stolte et al. |
| 2009/0286919 A1 | 11/2009 | Moller et al. |
| 2009/0312279 A1 | 12/2009 | Mookerjee et al. |
| 2010/0074083 A1 | 3/2010 | Shibuya et al. |
| 2010/0216890 A1 | 8/2010 | Lichtenberg et al. |
| 2010/0234460 A1 | 9/2010 | Foret et al. |
| 2010/0286270 A1 | 11/2010 | Foret et al. |
| 2010/0298190 A1 | 11/2010 | Molinaro et al. |
| 2011/0082248 A1 | 4/2011 | Butikofer |
| 2011/0117032 A1 | 5/2011 | Gilding |
| 2011/0130479 A1 | 6/2011 | Kramer et al. |
| 2011/0166259 A1 | 7/2011 | Butkofer |
| 2011/0207649 A1 | 8/2011 | Molinaro et al. |
| 2011/0216122 A1* | 9/2011 | Maruyama ............ C09D 125/14 347/20 |
| 2011/0269936 A1 | 11/2011 | Tets et al. |
| 2011/0294899 A1 | 12/2011 | Lang et al. |
| 2012/0070341 A1 | 3/2012 | Eder et al. |
| 2012/0071438 A1 | 3/2012 | Pedersen et al. |
| 2012/0094007 A1 | 4/2012 | Fehr et al. |
| 2012/0121723 A1 | 5/2012 | Mookerjee et al. |
| 2012/0171505 A1 | 7/2012 | Rohlf et al. |
| 2012/0270967 A1 | 10/2012 | Burckhardt et al. |
| 2013/0172436 A1 | 7/2013 | Fosco, Jr. et al. |
| 2013/0177475 A1 | 7/2013 | Finch |
| 2013/0261270 A1 | 10/2013 | Butikofer et al. |
| 2014/0011906 A1 | 1/2014 | Fosco, Jr. et al. |

FOREIGN PATENT DOCUMENTS

| | | |
|---|---|---|
| AU | 2007235922 B2 | 10/2007 |
| AU | 2009327174 B2 | 6/2010 |
| AU | 2010260586 B2 | 12/2010 |
| AU | 2011265527 A1 | 2/2012 |
| AU | 2011265527 B2 | 2/2012 |
| AU | 2012203225 A1 | 6/2012 |
| CA | 2422496 A1 | 3/2003 |
| CA | 2803702 A1 | 1/2012 |
| CA | 2823036 A1 | 7/2012 |
| EP | 1322156 B1 | 3/2006 |
| EP | 1741451 A1 | 1/2007 |
| EP | 1878769 A1 | 1/2008 |
| EP | 1652909 B1 | 3/2008 |
| EP | 2105450 A1 | 9/2009 |
| EP | 1322156 B3 | 12/2010 |
| EP | 1652909 B2 | 4/2011 |
| EP | 2520605 A1 | 11/2012 |
| GB | 773833 | 5/1957 |
| GB | 783882 | 10/1957 |
| GB | 2497389 A | 6/2013 |
| GB | 2501341 A | 10/2013 |
| WO | 2002061026 A1 | 8/2002 |
| WO | WO 2002061026 A1 * | 8/2002 |
| WO | 03099006 A1 | 12/2003 |
| WO | 2003099006 A1 | 12/2003 |
| WO | 2004052959 A1 | 6/2004 |
| WO | 2004101726 A2 | 11/2004 |
| WO | 2007116051 A1 | 10/2007 |
| WO | 2008031087 A1 | 3/2008 |
| WO | 2008031090 A1 | 3/2008 |
| WO | 2008085446 A2 | 7/2008 |
| WO | 2008085446 A3 | 7/2008 |
| WO | 2009028891 A2 | 3/2009 |
| WO | 2009040597 A1 | 4/2009 |
| WO | 2009118153 A1 | 10/2009 |
| WO | 2009150212 A1 | 12/2009 |
| WO | 2009150219 A1 | 12/2009 |
| WO | 2010010345 A2 | 1/2010 |
| WO | 2010069898 A1 | 6/2010 |
| WO | 2010147485 A1 | 12/2010 |
| WO | 2011015881 A2 | 2/2011 |
| WO | 2011039172 A2 | 4/2011 |
| WO | 2011069846 A1 | 6/2011 |
| WO | 2012001400 A1 | 1/2012 |
| WO | 2012001400 A4 | 1/2012 |
| WO | 2012010197 A1 | 1/2012 |
| WO | WO 2012010197 A1 * | 1/2012 |
| WO | 2012038914 A2 | 3/2012 |
| WO | 2012038915 A2 | 3/2012 |
| WO | 2012080265 A1 | 6/2012 |
| WO | 2012091891 A2 | 7/2012 |
| WO | 2012091891 A3 | 7/2012 |
| WO | 2012123273 A1 | 9/2012 |
| WO | 2012158425 A1 | 11/2012 |
| WO | 2013012797 A2 | 1/2013 |
| WO | 2013061082 A1 | 5/2013 |
| WO | 2013098547 A1 | 7/2013 |
| WO | 2013156371 A1 | 10/2013 |

OTHER PUBLICATIONS

Ecolab USA Inc., PCT/US2016/052121 filed Sep. 16, 2016, "The International Search Report and the Written Opinion of the International Searching Authority, or the Declaration and the Written Opinion of the International Searching Authority", 13 pages, dated Dec. 25, 2016.

European Patent Office, "Supplementary European Search Report" issued in connection to International Application No. 18168680.9-1110 dated Jul. 2, 2018.

European Patent Office, "Extended European Search Report", issued in connection to International Application No. 16847376.7-1110 dated Apr. 4, 2019.

* cited by examiner

TRIAMINE SOLIDIFICATION USING DIACIDS

CROSS-REFERENCE TO RELATED APPLICATIONS

This application is a Continuation Application of U.S. Ser. No. 15/267,363, filed on Sep. 16, 2016, which claims priority and is related to U.S. Provisional Application Ser. No. 62/219,781, filed on Sep. 17, 2015, all of which are hereby expressly incorporated herein by reference including, without limitation, the specification, claims, and abstract, as well as any figures, tables, or drawings thereof.

FIELD OF THE INVENTION

The invention relates to stable, solid triamine antimicrobial, sanitizing and disinfectant compositions, including for example, cast, extruded and pressed solid compositions. Ready-to-use solutions can be obtained by dissolving the solid triamine compositions with water. Methods of use for cleaning, disinfecting, sanitizing, rinsing and/or lubricating are disclosed. Beneficially, the solid triamine compositions provide at least substantially similar or superior performance and micro efficacy to liquid formulations.

BACKGROUND OF THE INVENTION

Multiple soils are present in institutional and other settings requiring the removal of, cleaning, sanitizing and/or disinfecting of protein, fat and oil, and starch-based soils. Often these soils end up on hard surfaces and soft surfaces and can be difficult to remove, requiring aggressive cleaning products. There is an ongoing need for effective cleaning products.

Liquid triamine antimicrobial compositions may provide cleaning, disinfecting, sanitizing, rinsing and/or lubricating benefits. However, the amine providing antimicrobial activity (N,N-Bis(3-aminopropyl)dodecylamine) in its unaltered state is difficult to formulate into solid compositions. The liquid form of the amines conventionally requires use of diluted liquid compositions and presents numerous barriers to solid formulation of the triamine antimicrobial compositions. Further, the formulation of solid triamine composition has required the addition of numerous functional ingredients which dilute the concentration of triamine in solid antimicrobial conditions, thus imparing the efficacy of the composition. Accordingly, it is an objective of the claimed invention to develop a solid triamine antimicrobial, sanitizing and disinfectant composition for cleaning, disinfecting, sanitizing, rinsing and/or lubricating. In an aspect of the invention, the solid products of the present invention are more convenient, safe and economical than liquid products, because they do not spill or splash, have reduced manufacturing and distribution costs, and require less storage space among other benefits. As such, it is a further objective of the claimed invention to develop methods of solidification of a composition consisting essentially of triamine and an acid.

A further object of the invention is to provide solid compositions having minimal water content to allow pressed solid formulations.

Other objects, advantages and features of the present invention will become apparent from the following specification taken in conjunction with the accompanying drawings.

BRIEF SUMMARY OF THE INVENTION

In an embodiment, the present invention provides solid triamine compositions, a kit comprising a solid triamine composition an instructions for dilution and use, methods of making solid triamine compositions, and methods of using the same.

In an embodiment, a solid triamine composition comprises: between about 10 and 99 wt-% triamine; and between about 1 and 50 wt-% diacid. In a further embodiment, the ratio of the diacid to the triamine is from about 1:10 to about 1:1. In a further embodiment, the triamine and diacid are combined in at least a partially neutralized solid composition, and wherein the composition remains solid below 50° C.

In an embodiment, a kit comprises: solid triamine composition comprising triamine and a diacid as disclosed herein; and instructions for dilution and use.

In an embodiment, a method of making a solid triamine composition comprises: at least partially neutralizing a triamine; reacting the biocidal triamine with a diacid to generate an amine salt; and solidifying the composition. In an embodiment, the solid composition remains solid below 50° C. In a further embodiment, the ratio of the diacid to the triamine is from about 1:10 to about 1:1.

In an embodiment, a method of cleaning, sanitizing or disinfecting comprises: generating a use solution of a solid triamine composition comprising a triamine and a diacid as disclosed herein, wherein the use solution provides between about 1 ppm to about 1000 ppm triamine, and between about 1 ppm to about 500 ppm diacid; and contacting an article or surface with the use solution for cleaning, sanitizing, or disinfecting.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE PREFERRED EMBODIMENT

The present invention relates to solid triamine antimicrobial, sanitizing and disinfecting, cleaning, rinsing and/or lubricating compositions. The compositions have advantages over conventional liquid triamine compositions, including for example, minimized costs for transportation and shipment, generation of use solutions at a point of use, and the like.

The embodiments of this invention are not limited to particular compositions, methods of using the same and methods of making the same, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

An "antiredeposition agent" refers to a compound that helps keep suspended in water instead of redepositing onto the object being cleaned. Antiredeposition agents are useful in the present invention to assist in reducing redepositing of the removed soil onto the surface being cleaned.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces, and further include instruments.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 3 log reduction and more preferably a 5-log order reduction. These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "soil" or "stain" refers to a non-polar oily substance which may or may not contain particulate matter such as mineral clays, sand, natural mineral matter, carbon black, graphite, kaolin, environmental dust, etc.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both.

The term "threshold agent" refers to a compound that inhibits crystallization of water hardness ions from solution, but that need not form a specific complex with the water hardness ion. Threshold agents include but are not limited to a polyacrylate, a polymethacrylate, an olefin/maleic copolymer, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

Solid Compositions

Exemplary ranges of the solid triamine compositions according to the invention are shown in Tables 1A-1C in weight percentage of the solid compositions.

TABLE 1A

| Material | First Exemplary Range wt-% | Second Exemplary Range wt-% | Third Exemplary Range wt-% | Fourth Exemplary Range wt-% |
| --- | --- | --- | --- | --- |
| Triamine | 10-99 | 20-90 | 50-90 | 10-50 |
| Solid acid | 1-60 | 2.5-40 | 5-40 | 2.5-20 |
| Additional Functional Ingredients (e.g. chelants, enzymes) | 0-65 | 0-50 | 0-25 | 15-50 |

TABLE 1B

| Material | First Exemplary Range wt-% | Second Exemplary Range wt-% | Third Exemplary Range wt-% |
| --- | --- | --- | --- |
| Triamine | 10-99 | 20-90 | 50-90 |
| Solid acid | 1-50 | 2.5-40 | 5-40 |
| Additional Functional Ingredients | 0-65 | 0-50 | 0-25 |
| Enzymes | 0.01-10 | 0.1-10 | 0.1-5 |

TABLE 1C

| Material | First Exemplary Range wt-% | Second Exemplary Range wt-% | Third Exemplary Range wt-% |
| --- | --- | --- | --- |
| Triamine | 10-99 | 10-80 | 10-50 |
| Solid acid | 1-50 | 2.5-40 | 5-40 |
| Additional Functional Ingredients | 0-50 | 0-25 | 0-15 |
| Chelant | 0.1-65 | 1-65 | 10-65 |

Further exemplary ranges of the solid triamine compositions particularly suitable for antimicrobial, sanitizing and disinfectant compositions according to the invention are shown in Tables 2A-2C in weight percentage of the solid compositions.

TABLE 2A

| Material | First Exemplary Range wt-% | Second Exemplary Range wt-% | Third Exemplary Range wt-% |
| --- | --- | --- | --- |
| Triamine | 10-99 | 10-70 | 20-50 |
| Solid acid | 1-50 | 2.5-40 | 5-20 |
| Additional Functional Ingredients (e.g. chelant, enzymes) | 0-90 | 10-80 | 20-75 |

TABLE 2B

| Material | First Exemplary Range wt-% | Second Exemplary Range wt-% | Third Exemplary Range wt-% |
| --- | --- | --- | --- |
| Triamine | 10-99 | 10-70 | 20-50 |
| Solid acid | 1-50 | 2.5-40 | 5-20 |
| Additional Functional Ingredients | 0-90 | 10-80 | 20-75 |
| Enzymes | 0.01-10 | 0.1-10 | 0.1-5 |

TABLE 2C

| Material | First Exemplary Range wt-% | Second Exemplary Range wt-% | Third Exemplary Range wt-% |
| --- | --- | --- | --- |
| Triamine | 10-99 | 10-70 | 20-50 |
| Solid acid | 1-50 | 2.5-40 | 5-20 |
| Additional Functional Ingredients | 0-90 | 10-80 | 20-75 |
| Chelant | 0.1-65 | 1-60 | 10-60 |

Beneficially, the solid triamine compositions are at least partially neutralized, allowing activity of 90% and greater of the biocidal triamine, and provide at least substantially similar or superior performance and micro efficacy to liquid formulations.

As referred to herein a "solid" composition is that which remains solid at temperatures up to about up to about 100° F. (45° C.), or preferably up to about 122° F. (50° C.). Preferably, the solid composition of the present invention may form stable and/or rigid compositions. In other aspects, the solid composition may be a powder. The solid composition may be present in different shapes, for example in form of a block or a pressed solid.

The solid compositions may be provided in varying sizes and may be suitable for single or multiple use applications. In an exemplary aspect, the total weight of a single dosage use form of said solid composition of the present invention can be for example ≥0.005 kg to <1 kg, preferably ≥0.005 kg to <0.25 kg. In a further exemplary aspect, the total weight of a multiple use form of said solid composition of the present invention can be for example ≥0.5 kg to <15 kg, preferably ≥1 kg to <105 kg.

In an aspect the ratio of the acid to triamine is from about 1:10 to about 1:1, from about 1:10 to about 1:5, from about 1:5 to about 1:3, or from about 1:3 to about 1:1. In a further aspect, the ratio of the acid to the triamine can be any combination below the 1:10 ratio, including for example 1:1, 1:0.5, etc. According to the invention the biocidal triamine is the dominant species in the solid compositions. In a preferred aspect, the ratio of acid to triamine is from about 1:2.5 to about 1:2. Without being limited to a particular mechanism of action the ratio of triamine to acid impacts the stability of the solid composition generated. In an aspect, a higher acid concentration results in a greater water content from the neutralization step in the generated solid biocidal triamine composition and may impact the type of solid generated. For example, a solid biocidal triamine composition having a lower water content is optimal for producing pressed solids according to the invention. However, solid biocidal triamine compositions having increased water content remain suitable for use in pressed, cast and/or extruded solids.

According to embodiments of the invention, the solid triamine compositions are partially neutralized compositions. In an aspect, the solid compositions have a pH from about 6 to about 10, from about 6.5 to about 8, and preferably from about 6.5 to about 7.5 or about 7. In an aspect of the invention more acidic compositions (pH below 7) achieve stable solid compositions using a higher acid concentration. In yet other aspects, lower concentrations of acid (providing a pH of at least 7) is preferred for optimal micro efficacy.

The degree of hardness of the solid compositions generated according to the invention may range from that of a flowable or free-flowing powder to a fused solid product which is relatively dense and hard, to a consistency characterized as being a hardened paste. In addition, the term "solid" refers to the state of the triamine composition under the expected conditions of storage and use of the solid triamine composition. In general, it is expected that the solid triamine composition will remain in solid form when exposed to temperatures of up to approximately 100° F. and preferably up to approximately 122° F.

Beneficially, the solid triamines of varying solid forms generated according to the methods of the invention are substantially homogeneous with regard to the distribution of ingredients throughout its mass and are dimensionally stable. As referred to herein, dimensionally stable solids have less than 3% growth at 104° F., preferably less than 2% growth at 104° F., or preferably less than 3% growth at 122° F. Each reference to the measurement of dismentional stability is at the mentioned temperature and at a relative humidity between about 40-70%.

According to the embodiments of the invention the solid triamine compositions can be utilized for any pressed, extruded, block and/or cast solid compositions. Still further, according to the invention the composition can be utilized for any molded or formed solid pellet, block, tablet, powder, granule, flake or the formed solid can thereafter be ground or formed into a powder, granule, or flake.

Biocidal Triamine

The solid triamine compositions according to the invention include at least one biocidal triamine. As referred to herein the biocidal triamine may be referred to as a bis (3-aminopropyl) dodecylamine, 1,3-propanediamine, N-(3-aminopropyl)-N-dodecylamine, Dodecylamine, or N,N-bis (3-aminopropyl) laurylamine, or may be represented by the formula

(1)

wherein R is a linear or branched alkyl residue with C1-22, C1-C18, or C1-12. The residue R of the amines can be saturated, unsaturated, mono- or polyunsaturated. In a preferred aspect R is a straight chain alkyl group, preferably C1-C12, or more preferably $C_{12}H_{25}$. Such amines can be produced according to processes known in the literature and/or are available as commercial products. A commercially available biocidal triamine is available under the tradename Lonzabac® sold by Lonza Inc. Further commercially available biocidal triamines include N-coco-1,3-propylene diamine, N-oleyl-1,3-propylene diamine, N-tallow-1,3-propylene diamine, mixtures thereof, or salts thereof, such N-alkyl-1,3-propylene diamines are available from Akzo Chemie America and Armak Chemicals.

As referred to herein the biocidal triamine may further be described as an alkylamine. The biocidal triamine may further be described as an alkylamine of mono-, di- and/or polyamines. Exemplary biocidal triamine may include, for example, those selected from the following formulas:

(1a)

(1b)

(1C)

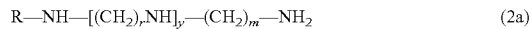
(2a)

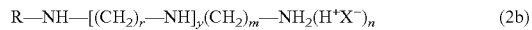
(2b)

(3a)

$R_2$—$NY_2^+X"$ (3b)

wherein, R is a linear or branched alkyl residue, preferably with 6 to 22 C atoms, wherein Y independently represents hydrogen or a methyl group, wherein X" is an equivalent of an anion, selected from the group comprising an amidosulfonate, nitrate, halide, sulfate, hydrogen carbonate, carbonate, phosphate, hydroxide, carboxylate, and/or organic acid, wherein m, r, and y independently represent an integer ranging from 1 to 6, and wherein n is an integer ranging from 1 to 2+y.

In an aspect, the residue R of the amines can be a linear or branched alkyl residue with 6 C atoms to 22 C atoms, preferably 8 C atoms to 20 C atoms, further preferred 10 C atoms to 18 C atoms and also preferred 12 C atoms to 16 C atoms or 14 C atoms. In a further aspect, the residue R of the amines can be saturated, unsaturated, mono- or polyunsaturated. In a still further aspect, preferred amines include amines, wherein R is C8 to C18 alkyl, most preferred C8 to C12 alkyl. In an aspect, m, r, and y independently represent an integer ranging from 2 to 5 or 3 to 4 and most preferred 3.

In an aspect, dialkylamines, trialkylamines, alkyldiamines and/or alkyltriamines can be preferred, selected from the group comprising cocopropylenediamine, oleyldipropylenetriamine, tallowdipropylenetriamine, oleylpropylenediamine, tallow-dipropylenetriamine, oleyltripropylenetetramine, N-3-aminopropyl-N-dodecyl-1,3-propane-diamine and/or a salt with X" thereof. The anion X" can be selected from the group comprising an amidosulfonate, nitrate, halide, sulfate, hydrogen carbonate, carbonate, phosphate, hydroxide, carboxylate, and/or organic acid.

As referred to herein the biocidal triamine may further be described as an alkanolamine. Exemplary biocidal triamine may include, for example, those selected from the following formulas:

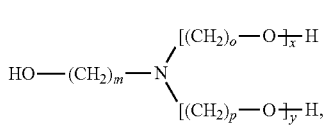

(4)

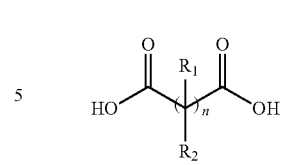

(a)

where m and, if present, o and p independently of one another have the value 2 or 3, and x and y independently of one another have the value 0 or 1, or a corresponding salt; in the mass ratio (I):(II) of 20:1 to 1:20. Alkyl, here and hereinafter, is taken to mean in each case unbranched or branched alkyl groups of the specified number of carbons, and particularly preferably those having an even number of carbon atoms.

Exemplary alkanolamines are in principle all ethanolamines and propanolamines, in particular mono-ethanolamine, diethanolamine, triethanolamine and 3-amino-1-propanol. In an aspect, a preferred alkanolamine compounds has a primary amino group, that is to say using monoethanolamine and 3-amino-1-propanol.

In an aspect, the biocidal amines for use according to the invention may include any mixture of different amines, or alkylamines, or alkanolamines.

As referred to herein, the biocidal amines may correspond to any of the general formulas, and can be produced according to processes known in the literature and/or are available as commercial products.

In an aspect, the biocidal triamine concentration may be dependent upon the desired pH of the use solution generated from the solid formulation. It is an unexpected benefit of the present invention that the triamine compositions with high active concentrations of the biocidal triamines are solids.

In an aspect, the solid triamine compositions include from about 10 wt-% to about 99 wt-% biocidal triamine, from about 20 wt-% to about 90 wt-% biocidal triamine, or from about 50 wt-% to about 90 wt-% biocidal triamine. In a preferred aspect, the solid triamine compositions including substantial amounts of additional functional ingredients for suitable antimicrobial, sanitizing and disinfectant compositions include from about 10 wt-% to about 99 wt-% biocidal triamine, from about 10 wt-% to about 70 wt-% biocidal triamine, or from about 20 wt-% to about 50 wt-% biocidal triamine. In still other aspects including those where additional functional ingredients are included in the formulations, the solid triamines include from about 5 wt-% to about 75 wt-% biocidal triamine, from about 5 wt-% to about 50 wt-% biocidal triamine, or from about 10 wt-% to about 25 wt-% biocidal triamine. Without being limited according to the invention, all ranges recited are inclusive of the numbers defining the range and include each integer within the defined range.

Acids

The solid triamine compositions according to the invention include at least one acid. The acid may be organic or inorganic. The acid is preferably an organic acid. In an aspect the acid may be an organic monocarboxylic acid or an organic dicarboxylic acid. In an aspect, the acid is a solid acid, preferably a diacid.

In an aspect, the solid triamine composition comprises a diacid having the structure (a) as shown:

Wherein: $n=1\text{-}20$, $R_1$ is H, C1-C8 alkyl or COOH; $R_2$ is H, C1-C8 alkyl, $NH_2$, OH, or COOH, and $R_1$ and $R_2$ substitution occurs on at least one carbon within C1-C20 chain.

In an aspect, the solid triamine composition comprises a diacid having the structure (b) as shown:

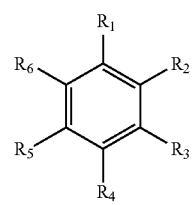

(b)

Wherein: $R_1$ and $R_2$ are each COOH; $R_3$, $R_4$, $R_5$ and $R_6$ independently are H, C1-C8 alkyl, OH, or $NH_2$; $R_1$ and $R_3$ are each COOH; $R_2$, $R_4$, $R_5$, and $R_6$ independently are H, C1-C8 alkyl, OH, or $NH_2$; $R_1$ and $R_4$ are each COOH; $R_2$, $R_3$, $R_5$, and $R_6$ independently are H, C1-C8 alkyl, OH, or $NH_2$; $R_1$ and $R_5$ are each COOH; $R_2$, $R_3$, $R_4$, and $R_6$ independently are H, C1-C8 alkyl, OH, or $NH_2$; or $R_1$ and $R_6$ are each COOH; $R_2$, $R_3$, $R_4$, and $R_5$ independently are H, C1-C8 alkyl, OH, or $NH_2$.

In an aspect, the solid triamine composition comprises a diacid having the structure (c) as shown:

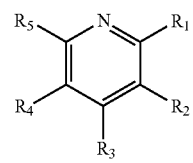

(c)

Wherein: $R_1$ and $R_2$ are COOH; $R_3$, $R_4$, and $R_5$ independently are H, C1-C8 alkyl, OH, or $NH_2$; $R_1$ and $R_3$ are COOH; $R_2$, $R_4$, $R_5$ independently are H, C1-C8 alkyl, OH, or $NH_2$; $R_1$ and $R_4$ are COOH; $R_2$, $R_3$, $R_5$ independently are H, C1-C8 alkyl, OH, or $NH_2$; or $R_1$ and $R_5$ are COOH; $R_2$, $R_3$, $R_4$ independently are H, C1-C8 alkyl, OH, or $NH_2$.

In an aspect, the solid triamine composition comprises at least one diacid having the structures as shown and described as (a), (b), (c) or combinations thereof.

Particularly preferred acids include citric acid, tartaric, malic, maleic, malonic, succinic, adipic, aspartic, glutamic, dipicolinic, and dodecanoic acid. Particularly preferred acids include the following:

Citric acid, 3-carboxy-3-hydroxypentanedioic acid, 2-hydroxy-1,2,3-propanetricarboxylic acid, having the formula:

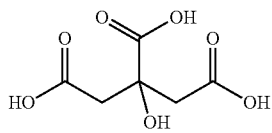

Tartaric acid, 2,3-dihydroxybutanedioic acid, 2,3-dihydroxysuccinic acid, threaric acid, racemic acid, uvic acid, paratartaric acid, having the formula:

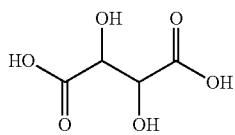

Malic acid, 2-hydroxybutanedioic acid, having the formula:

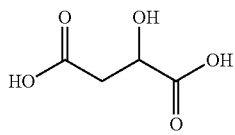

Maleic acid, (Z)-butenedioic acid, cis-butenedioic acid, malenic acid, maleinic acid, toxilic acid, having the formula:

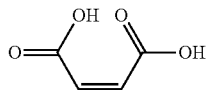

Glutamic acid, 2-aminopentanedioic acid, 2-aminoglutaric acid, having the formula:

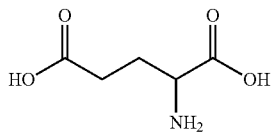

Dipicolinic acid, pyridine-2,6-dicarboxylic acid, 2,6-pyridinedicarboxylic acid, having the formula:

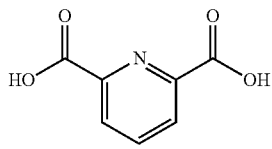

Succinic acid, Butanedioic acid, ethane-1,2-dicarboxylic acid, having the formula:

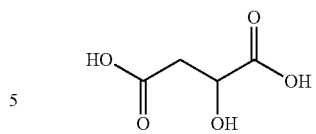

Adipic acid, hexanedioic acid, hexane-1,6-dicarboxylic acid, hexane-1,6-dioic acid, having the formula:

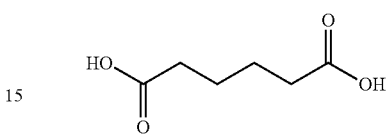

Dodecanedioic acid —$C_{12}H_{22}O_4$, having the formula:

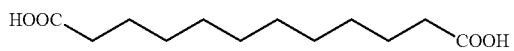 [SMILES: O=C(O)CCCCCCCCCCC(=O)O]

Additional exemplary acids may include those organic acids selected from the group consisting of acetic acid, formic acid, propionic acid, citric acid, i.e., 2-hydroxy-1,2,3-propanetricarboxylic acid, lactic acid, tartaric acid, glycolic acid, salicylic acid, fumaric acid, malic acid, itaconic acid, ascorbic acid, succinic acid and benzoic acid.

Without being limited according to a mechanism of action, the acid preferably provides a water-soluble salt of the triamine. In a preferred aspect, the acid generates a water-soluble salt of the triamine in a solid formulation.

In an aspect, the solid triamine compositions include from about 1 wt-% to about 50 wt-% solid acid, from about 5 wt-% to about 40 wt-% solid acid, or from about 10 wt-% to about 35 wt-% solid acid. In a preferred aspect, the solid triamine compositions including substantial amounts of additional functional ingredients for suitable antimicrobial, sanitizing and disinfectant compositions include from about 1 wt-% to about 50 wt-% solid acid, from about 5 wt-% to about 40 wt-% solid acid, or from about 5 wt-% to about 20 wt-% solid acid. In still other aspects, including those where additional functional ingredients are included in the formulations, the solid triamines include from about 1 wt-% to about 35 wt-% acid, from about 1 wt-% to about 20 wt-% acid, or from about 2.5 wt-% to about 20 wt-% acid. Without being limited according to the invention, all ranges recited are inclusive of the numbers defining the range and include each integer within the defined range.

Water

The solid composition according to the present invention can contain a small amount of water. For example, components of the solid composition such as the biocidal triamine (or other functional ingredients) may comprise water. Preferrably water is not added into the composition and based on the total weight of the solid composition there is a water content in the range of ≥0 wt-% to <5 wt-%, preferably ≥0 wt-% to <2.5 wt-%, further preferred ≥0 wt-% to <1 wt-%, furthermore preferred ≥0 wt-% to <0.5 wt-%. In some aspects, including those where additional functional ingredients are included in the formulations, components with additional water content can be included in the composition, and preferably total water content of the solid formulations is less than about 10 wt-%, less than about 9 wt-%, less than about 8 wt-%, less than about 7.5 wt-%, less than about 7 wt-%, less than about 6 wt-%, or less than about 5 wt-%. Without being limited according to the invention, all ranges recited are inclusive of the numbers defining the range and include each integer within the defined range.

Additional Functional Ingredients

The components of the solid triamine compositions can optionally be combined with various functional components suitable for use in disinfectant applications. In some embodiments few or no additional functional ingredients are disposed therein the solid triamine compositions. In other embodiments, the solid triamine compositions include at least one additional functional ingredient. Additional functional ingredients provide desired properties and functionalities to the compositions. For the purpose of this application, the term "functional ingredient" includes a material that when formulated into the solid composition or when dispersed or dissolved in a use and/or concentrate solution of the solid triamine compositions, provides a beneficial property in a particular disinfectant application of use. Additional functional ingredients may provide formulation benefits and/or performance benefits.

Some particular examples of functional materials are discussed in more detail below, although the particular materials discussed are given by way of example only, and that a broad variety of other functional ingredients may be used. For example, many of the functional materials discussed below relate to materials used in cleaning and disinfectant applications. However, other embodiments may include functional ingredients for use in other applications.

In preferred embodiments, the compositions do not include or are substantially free of boric acid or boric acid salts.

In other embodiments, the solid triamine compositions may include enzymes, additional hardening or solidifying agents, defoaming agents, anti-redeposition agents, bleaching agents, solubility modifiers, dispersants, rinse aids, metal protecting agents, stabilizing agents, corrosion inhibitors, additional sequestrants and/or chelating agents, fragrances and/or dyes, rheology modifiers or thickeners, hydrotropes or couplers, buffers, solvents and the like.

In some aspects, the solid triamine compositions include from about 0 wt-% to about 50 wt-% additional functional ingredients, from about 0 wt-% to about 25 wt-% additional functional ingredients, or from about 0 wt-% to about 15 wt-% additional functional ingredients. In a preferred aspect, the solid triamine compositions including substantial amounts of additional functional ingredients for suitable antimicrobial, sanitizing and disinfectant compositions include from about 0 wt-% to about 90 wt-% additional functional ingredients, from about 10 wt-% to about 80 wt-% additional functional ingredients, or from about 20 wt-% to about 75 wt-% additional functional ingredients. Without being limited according to the invention, all ranges recited are inclusive of the numbers defining the range and include each integer within the defined range.

Enzymes

In some embodiments, the solid triamine compositions may further include an enzyme, but may include any number of enzymes. The enzyme may include a protease, amylase, lipase, gluconase, cellulase, peroxidase, a combination, or other enzymes. The system preferably includes at least one lipase. The enzymes may be vegetable, animal, bacterial, fungal or yeast enzymes, or genetic variations thereof. The enzyme should be selected based on factors like pH, stability, temperature, and compatibility with materials found in detergent compositions and cleaning applications. Preferred enzymes have activity in the pH range of about 2-14 or 6-12 and at temperatures from about 20 C to 80 C. The enzyme may be a wild type enzyme or a recombinant enzyme. Preferred enzymes have a broad spectrum of activity and a high tolerance for materials found in cleaning compositions like alkalinity, acidity, chelating agents, sequestering agents, and surfactants.

The enzyme concentration in the system depends on the particular enzyme's activity. The enzyme concentration can range from about 0 to about 10.0 wt-%, about 0.1 to about 5.0 wt-%, or about 0.5 to about 2.0 wt-% of a sold composition. Without being limited according to the invention, all ranges recited are inclusive of the numbers defining the range and include each integer within the defined range. A person skilled in the art will be able to determine the enzyme concentration after selecting a desired enzyme based on the enzyme's activity and profile.

Exemplary enzymes are listed below, and description of the same is incorporated by reference in its entirety with respect to exemplary enzymes from U.S. Pat. Nos. 8,211,849 and 8,227,397:

Lipase

Lipase isolated from: Pseudomona, *Pseudomonas stutzeri* ATCC 19.154, *Humicola, Humicola lanuginose* (reproduced recombinantly in *Aspergillus oryzae*), *Chromobacter viscosum, Pseudomonas gladioli, Humicola lanuginose*, and the like.

Protease

Protease isolated from: *Bacillus lentus, Bacillus licheniformis, Bacillus amyloliquefaciens*, and the like.

Amylase

Amylase isolated from: *Bacillus licheniformis, Bacillus amyloliquefaciens, Bacillus subtilis, Bacillus stearothermophilus*, and the like.

Cellulase

Cellulase isolated from: *Humicola insolens, Humicola* strain DSM 1800, cellulase 212-producing fungus of the genus *Aeromonas*, cellulase extracted from the hepatopancrease of the marine mollusk Dorabella Auricula Solander, and the like.

Other Enzymes

Peroxidase (horseradish peroxidase)

Ligninase

Haloperoxidase (chloroperoxidase, bromoperoxidase)

Gluconase

Chelants

In some embodiments, the solid triamine compositions may further include a chelant. Chelation herein means the binding or complexation of a bi- or multidentate ligand. These ligands, which are often organic compounds, are called chelants, chelators, chelating agents, and/or sequestering agent. Chelating agents form multiple bonds with a single metal ion. Chelants, are chemicals that form soluble, complex molecules with certain metal ions, inactivating the ions so that they cannot normally react with other elements or ions to produce precipitates or scale. The ligand forms a chelate complex with the substrate. The term is reserved for complexes in which the metal ion is bound to two or more atoms of the chelant.

Suitable aminocarboxylic acid type chelants include the acids, or alkali metal salts thereof. Some examples of aminocarboxylic acid materials include amino acetates and salts thereof. Some examples include the following: N-hydroxyethylaminodiacetic acid; hydroxyethylenediaminetetraacetic acid, nitrilotriacetic acid (NTA); ethylenediaminetetraacetic acid (EDTA); N-hydroxyethylethylenediaminetriacetic acid (HEDTA); diethylenetriaminepentaacetic acid (DTPA); and alanine-N, N-diacetic acid; and the like; and mixtures thereof. Particularly useful aminocarboxylic acid materials containing little or no NTA and no phosphorus include: N-hydroxyethylaminodiacetic acid, ethylenediaminetetraacetic acid (EDTA), hydroxyethylenediaminetetraacetic acid, diethylenetriaminepentaacetic acid, N-hydroxyethyl-ethylenediaminetriacetic acid (HEDTA), diethylenetriaminepentaacetic acid (DTPA), methylglycinediacetic acid (MGDA), aspartic acid-N,N-diacetic acid (ASDA), glutamic acid-N,N-diacetic acid (GLDA), ethylenediaminesuccinic acid (EDDS), 2-hydroxyethyliminodiacetic acid (HEIDA), iminodisuccinic acid (IDS), 3-hydroxy-2,2'-iminodisuccinic acid (HIDS) and other similar acids having an amino group with a carboxylic acid substituent.

Other chelants include amino carboxylates include ethylenediaminetetra-acetates, N-hydroxyethylethylenediaminetriacetates, nitrilo-triacetates, ethylenediamine tetrapri-onates, triethylenetetraaminehexacetates, diethylenetriaminepentaacetates, and ethanoldi-glycines, alkali metal, ammonium, and substituted ammonium salts therein and mixtures therein. Suitable chelating agents can be selected from the group consisting of amino carboxylates, amino phosphonates, polyfunctionally-substituted aromatic chelating agents and mixtures thereof. Exemplary chelants include amino acids based chelants and preferably citrate, tartrate, and glutamic-N,N-diacetic acid and derivatives and/or phosphonate based chelants.

Other chelants include homopolymers and copolymers of polycarboxylic acids and their partially or completely neutralized salts, monomeric polycarboxylic acids and hydroxycarboxylic acids and their salts. Preferred salts of the above-mentioned compounds are the ammonium and/or alkali metal salts, i.e. the lithium, sodium, and potassium salts, and particularly preferred salts are the sodium salts, such as sodium sulfate.

Other compounds suitable for use as additional functional ingredients to reduce the water content of the solid composition may include sodium acetate and other anti-caking agents. These may be necessary due to the concentration of water introduced to the solid compositions by way of chelants, such as EDTA. In a preferred aspect, the additional functional ingredient is employed to reduce the total water content of the solid composition to less than about 10 wt-%, less than about 9 wt-%, less than about 8 wt-%, less than about 7.5 wt-%, less than about 7 wt-%, less than about 6 wt-%, or less than about 5 wt-% water. The chelant concentration in the system can range from about 0 to about 65 wt-%, 0.1 to about 50 wt-%, about 0.1 to about 50 wt-%, about 1 to about 40 wt-%, or about 10 to about 40 wt-% of the composition. Without being limited according to the invention, all ranges recited are inclusive of the numbers defining the range and include each integer within the defined range.

Defoaming Agents

In some embodiments, the solid triamine compositions may further include an additive like an antifoam agent. The antifoam agent is preferably selected from the variety of antifoams such as those of the silicon type and/or polypropylene glycol type. Antifoam agents can be selected from the group comprising silicones and/or other defoamers like defoaming surfactants. Suitable silicone based antifoam agents have a silicone compound as the active component. These are delivered as oil or a water based emulsion. The silicone compound consists preferably of an hydrophobic silica dispersed in a silicone oil. The silicone compound might also contain silicone glycols and other modified silicone fluids. Suitable ethylene glycol (EO) and/or propylene glycol (PO) based antifoam agents contain polyethylene glycol and polypropylene glycol copolymers. They are delivered as oils, water solutions, or water based emulsions. EO/PO copolymers normally have good dispersing properties.

The defoaming agent concentration in the system can range from about 0 to about 50 wt-%, about 0.01 to about 30 wt-%, or about 0.1 to about 30 wt-%. Without being limited according to the invention, all ranges recited are inclusive of the numbers defining the range and include each integer within the defined range.

Surfactants

In some embodiments, the solid triamine compositions may further include a surfactant. Surfactants suitable for use with the compositions of the present invention include, but are not limited to, nonionic surfactants, cationic surfactants, and anionic surfactants based upon the solubility of the biocidal triamines. In some embodiments, the solid triamine compositions of the present invention include about 5 wt-% to about 50 wt-% of a surfactant, from about 5 wt-% to about 25 wt-% of a surfactant, or from about 5 wt-% to about 15 wt-% of a surfactant. Without being limited according to the invention, all ranges recited are inclusive of the numbers defining the range and include each integer within the defined range.

Nonionic Surfactants

Suitable nonionic surfactants suitable for use with the compositions of the present invention include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like.

The semi-polar type of nonionic surface active agents is another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

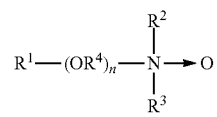

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Functional Siloxane Surfactants

The composition can also optionally include one or more functional polysiloxanes. For example, in some embodiments, a polyalkylene oxide-modified polydimethylsiloxane, nonionic surfactant or a polybetaine-modified polysiloxane amphoteric surfactant can be employed as an additive. Both, in some embodiments, are linear polysiloxane copolymers to which polyethers or polybetaines have been grafted through a hydrosilation reaction. Some examples of specific siloxane surfactants are known as SILWET® surfactants available from Union Carbide, ABIL® polyether or polybetaine polysiloxane copolymers available from Evonik Corporation, Tegopren® polyether polysiloxane copolymers available from Evonik Corporation and others described in U.S. Pat. No. 4,654,161 which is incorporated herein by reference. Preferred functional siloxane surfactants include, but are not limited Tegopren® 5831, Tegopren® 5840, Tegopren® 5847, Tegopren® 5852 and Tegopren® 5853. In some embodiments, the particular siloxanes used can be described as having, e.g., low surface tension, high wetting ability and excellent lubricity. For example, these surfactants are said to be among the few capable of wetting polytetrafluoroethylene surfaces. The siloxane surfactant employed as an additive can be used alone or in combination with a fluorochemical surfactant. In some embodiments, the fluorochemical surfactant employed as an additive optionally in combination with a silane, can be, for example, a nonionic fluorohydrocarbon, for example, fluorinated alkyl polyoxyethylene ethanols, fluorinated alkyl alkoxylate and fluorinated alkyl esters. Further description of such functional polydimethylsiloxones and/or fluorochemical surfactants are described in U.S. Pat. Nos. 5,880,088; 5,880,089; and 5,603,776, all of which patents are incorporated herein by reference.

In some embodiments, the composition may include functional polydimethylsiloxones in an amount in the range of up to about 10 wt.-%. For example, some embodiments may include in the range of about 0.1 to about 10 wt.-% of a polyalkylene oxide-modified polydimethylsiloxane or a polybetaine-modified polysiloxane, optionally in combination with about 0.1 to about 10 wt.-% of a fluorinated hydrocarbon nonionic surfactant.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula:

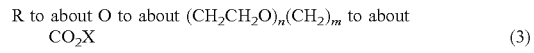

R to about O to about $(CH_2CH_2O)_n(CH_2)_m$ to about $CO_2X$ (3)

in which R is a $C_8$ to $C_{22}$ alkyl group or

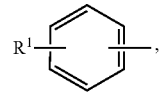

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a $C_8$-$C_{16}$ alkyl group. In some embodiments, R is a $C_{12}$-$C_{14}$ alkyl group, n is 4, and m is 1.

In other embodiments, R is

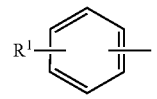

and $R^1$ is a $C_6$-$C_{12}$ alkyl group. In still yet other embodiments, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical).

Carboxylates are also available from Clariant, e.g. the product Sandopan® DTC, a $C_{13}$ alkyl polyethoxy (7) carboxylic acid.

Cationic Surfactants

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amine oxides, amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution.

The simplest cationic amines, amine salts and quaternary ammonium compounds can be schematically drawn thus:

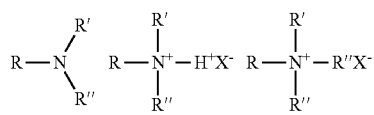

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", *Cosmetics & Toiletries*, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Cationic surfactants useful in the compositions of the present invention include those having the formula $R^1{}_m R^2{}_x Y_L Z$ wherein each $R^1$ is an organic group containing a straight or branched alkyl or alkenyl group optionally substituted with up to three phenyl or hydroxy groups and optionally interrupted by up to four of the following structures:

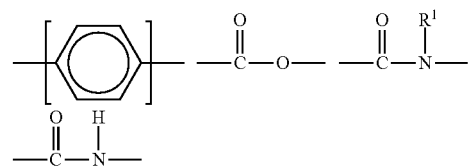

or an isomer or mixture of these structures, and which contains from about 8 to 22 carbon atoms. The $R^1$ groups can additionally contain up to 12 ethoxy groups. m is a number from 1 to 3. Preferably, no more than one $R^1$ group in a molecule has 16 or more carbon atoms when m is 2 or more than 12 carbon atoms when m is 3. Each $R^2$ is an alkyl or hydroxyalkyl group containing from 1 to 4 carbon atoms or a benzyl group with no more than one $R^2$ in a molecule being benzyl, and x is a number from 0 to 11, preferably from 0 to 6. The remainder of any carbon atom positions on the Y group are filled by hydrogens. Y is can be a group including, but not limited to:

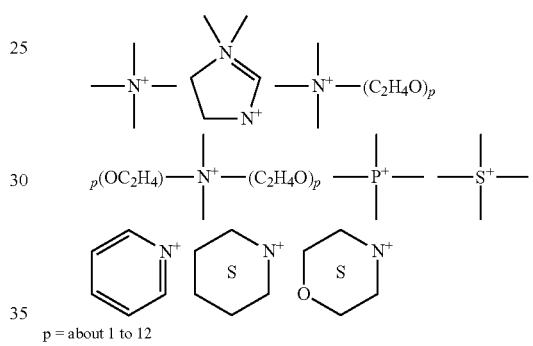

p = about 1 to 12 or a mixture thereof. Preferably, L is 1 or 2, with the Y groups being separated by a moiety selected from $R^1$ and $R^2$ analogs (preferably alkylene or alkenylene) having from 1 to about 22 carbon atoms and two free carbon single bonds when L is 2. Z is a water soluble anion, such as a halide, sulfate, methylsulfate, hydroxide, or nitrate anion, particularly preferred being chloride, bromide, iodide, sulfate or methyl sulfate anions, in a number to give electrical neutrality of the cationic component.

Hardening Agents

The solid compositions can also include a hardening agent to be employed with the solid triamines. A hardening agent is a compound or system of compounds, organic or inorganic, which significantly contributes to the uniform solidification of the composition. Preferably, the hardening agents are compatible with the cleaning agent and other active ingredients of the composition and are capable of providing an effective amount of hardness and/or aqueous solubility to the processed composition. The hardening agents should also be capable of forming a homogeneous matrix with the cleaning agent and other ingredients when mixed and solidified to provide a uniform dissolution of the cleaning agent from the solid detergent composition during use.

The amount of hardening agent included in the solid compositions will vary according to factors including, but not limited to: the type of solid composition being prepared, the ingredients of the solid composition, the intended use of the composition, the quantity of dispensing solution applied to the solid composition over time during use, the temperature of the dispensing solution, the hardness of the dispensing solution, the physical size of the solid composition, the concentration of the other ingredients, and the concentration of the solid triamines in the composition. It is preferred that the amount of the hardening agent included in the solid composition is effective to combine with the solid triamines and other ingredients of the composition to form a homogeneous mixture under continuous mixing conditions and a temperature at or below the melting temperature of the hardening agent.

The hardening agent may be an organic or an inorganic hardening agent. A preferred organic hardening agent is a polyethylene glycol (/po) compound. The solidification rate of solid compositions comprising a polyethylene glycol hardening agent will vary, at least in part, according to the amount and the molecular weight of the polyethylene glycol added to the composition. Examples of suitable polyethylene glycols include, but are not limited to: solid polyethylene glycols of the general formula $H(OCH_2CH_2)_m OH$, where n is greater than 15, particularly approximately 30 to approximately 1700. Typically, the polyethylene glycol is a solid in the form of a free-flowing powder or flakes, having a molecular weight of approximately 1,000 to approximately 100,000, particularly having a molecular weight of at least approximately 1,450 to approximately 20,000, more particularly between approximately 1,450 to approximately 8,000. The polyethylene glycol is present at a concentration of from approximately 0% to 75% by weight and particularly approximately 0.1% to approximately 15% by weight.

Inorganic hardening agents are hydratable inorganic salts, including, but not limited to: sulfates and bicarbonates. The inorganic hardening agents are present at concentrations of up to approximately 50% by weight, particularly approximately 5% to approximately 25% by weight, and more particularly approximately 5% to approximately 15% by weight. Urea particles can also be employed as hardeners in the solid compositions. The solidification rate of the compositions will vary, at least in part, to factors including, but not limited to: the amount, the particle size, and the shape of the urea added to the composition. For example, a particulate form of urea can be combined with a cleaning agent and other ingredients, and preferably a minor but effective amount of water. The amount and particle size of the urea is effective to combine with the cleaning agent and other ingredients to form a homogeneous mixture without the application of heat from an external source to melt the urea and other ingredients to a molten stage. It is preferred that the amount of urea included in the solid composition is effective to provide a desired hardness and desired rate of solubility of the composition when placed in an aqueous medium to achieve a desired rate of dispensing the cleaning agent from the solidified composition during use. In some embodiments, the composition includes between approximately 0% to approximately 90% by weight urea, particularly between approximately 5% and approximately 40% by weight urea, and more particularly between approximately 10% and approximately 30% by weight urea. The urea may be in the form of prilled beads or powder. Prilled urea is generally available from commercial sources as a mixture of particle sizes ranging from about 8-15 U.S. mesh, as for example, from Arcadian Sohio Company, Nitrogen Chemicals Division. A prilled form of urea is preferably milled to reduce the particle size to about 50 U.S. mesh to about 125 U.S. mesh, particularly about 75-100 U.S. mesh, preferably using a wet mill such as a single or twin-screw extruder, a Teledyne mixer, a Ross emulsifier, and the like.

Methods of Making

Solid triamine compositions are produced according to the methods of the invention. In an aspect, it is beneficial to formulate and deliver a solid composition for numerous reasons, including reduction of storage space and transport costs. In some aspects, the volume of the solid composition compared to a concentrated liquid equivalent can be reduced for example to at least 80%.

Another object of the present invention is directed to a method of manufacture of a solid composition of the present invention. All components that can be used in that process of manufacture are already defined for the solid composition of the present invention.

In an aspect, the triamine solids are made by a process comprising mixing at least the biocidal triamine and the acid to neutralize the biocidal triamine to a pH from about 7-10. The neutralization occurs during the mixing of the components in a mixing vessel. In an aspect, the alkaline pH of the biocidal triamine is neutralized prior to the solidification. In an aspect, the solidification reaction occurs over a period from about 1 hour to about 48 hours, or from about 1 hour to about 24 hours. In a preferred aspect, no water is added to the mixing vessel and the temperature for the reaction is between about 70° F. (21° C.) and about 130° F. (55° C.). In an aspect, mixing the components includes preferably mixing until a homogeneous mixture is obtained.

As one skilled in the art will ascertain, the mixing of the components, including the biocidal triamine and the acid, along with any number of optional additional functional ingredients, may include various sequences of adding the components to obtain the mixture. The methods of generating the solid compositions are not intended to be limited according to alterations in the process of manufacture involving the order of mixing the components described herein.

The methods of the present invention can produce a stable solid without employing a melt and solidification of the melt as in conventional casting. Forming a melt requires heating a composition to melt it. The heat can be applied externally or can be produced by a chemical exotherm (e.g., from mixing caustic (sodium hydroxide) and water). Heating a composition consumes energy. Handling a hot melt requires safety precautions and equipment. Further, solidification of a melt requires cooling the melt in a container to solidify the melt and form the cast solid. Cooling requires time and/or energy. In contrast, the present method can employ ambient temperature and humidity during solidification or curing of the present compositions.

The methods of the present invention can produce a stable solid without extruding to compress the mixture through a die. Conventional processes for extruding a mixture through a die to produce a solid cleaning composition apply high pressures to a solid or paste to produce the extruded solid. In contrast, the present method employs pressures on the solid of less than or equal to about 1000 psi or even as little as 1 psi. The solids of the present invention are held together not by mere compression but by a binding agent produced in the flowable solid and that is effective for producing a stable solid.

Any of a variety of flowable solids can be used in the method of the present invention. For example, in an embodiment, the flowable solid has a consistency similar to wet sand. Such a flowable solid can be compressed in a person's hand, like forming a snowball. However, immediately after forming it, a forceful impact (dropping or throwing) would return a hand compacted ball of the flowable solid to powder and other smaller pieces. In an embodiment, a flowable solid contains little enough water that compressing the powder at several hundred psi does not squeeze liquid water from the solid. In certain embodiments, the present flowable solid can be a powder or a wetted powder.

Solid compositions can be made by merely blending the biocidal triamine with the diacids in preferred ratios to obtain solid compositions. Pelletized materials can be manufactured by compressing the solid granular or agglomerated materials in appropriate pelletizing equipment to result in appropriately sized pelletized materials. Solid block and cast solid block materials can be made by introducing into a container either a prehardened block of material or a castable liquid that hardens into a solid block within a container. Preferred containers include disposable plastic containers or water soluble film containers. Other suitable packaging for the composition includes flexible bags, packets, shrink wrap, and water soluble film such as polyvinyl alcohol.

The solid compositions may be formed using a batch or continuous mixing system. In an exemplary embodiment, a single- or twin-screw extruder is used to combine and mix one or more components at high shear to form a homogeneous mixture. In some embodiments, the processing temperature is at or below the melting temperature of the components. The processed mixture may be dispensed from the mixer by forming, casting or other suitable means, whereupon the detergent composition hardens to a solid form. The structure of the matrix may be characterized according to its hardness, melting point, material distribution, crystal structure, and other like properties according to known methods in the art. Generally, a solid composition processed according to the method of the invention is substantially homogeneous with regard to the distribution of ingredients throughout its mass and is dimensionally stable.

In an extrusion process, liquid and solid components are introduced into final mixing system and are continuously mixed until the components form a substantially homogeneous semi-solid mixture in which the components are distributed throughout its mass. The mixture is then discharged from the mixing system into, or through, a die or other shaping means. The product is then packaged. In an exemplary embodiment, the formed composition begins to harden to a solid form in between approximately 1 minute and approximately 3 hours. Particularly, the formed composition begins to harden to a solid form in between approximately 1 minute and approximately 2 hours. More particularly, the formed composition begins to harden to a solid form in between approximately 1 minute and approximately 20 minutes.

In a casting process, liquid and solid components are introduced into the final mixing system and are continuously mixed until the components form a substantially homogeneous liquid mixture in which the components are distributed throughout its mass. In an exemplary embodiment, the components are mixed in the mixing system for at least approximately 60 seconds. Once the mixing is complete, the product is transferred to a packaging container where solidification takes place. In an exemplary embodiment, the cast composition begins to harden to a solid form in between approximately 1 minute and approximately 3 hours. Particularly, the cast composition begins to harden to a solid form in between approximately 1 minute and approximately 2 hours. More particularly, the cast composition begins to harden to a solid form in between approximately 1 minute and approximately 20 minutes.

In a pressed solid process, components are combined under pressure. In a pressed solid process, flowable solids of the compositions are placed into a form (e.g., a mold or container). The method can include gently pressing the flowable solid in the form to produce the solid composition. Pressure may be applied by a block machine or a turntable press, or the like. Pressure may be applied at ranges from about 1 to about 2000 psi, or about 1 to about 1000 psi depending upon the block shape and cylinder pressure. In certain embodiments, the methods can employ pressures as low as greater than or equal to about 1 psi, greater than or equal to about 2, greater than or equal to about 5 psi, or greater than or equal to about 10 psi. As used herein, the term "psi" or "pounds per square inch" refers to the actual pressure applied to the flowable solid being pressed and does not refer to the gauge or hydraulic pressure measured at a point in the apparatus doing the pressing. The method can include a curing step to produce the solid composition. As referred to herein, an uncured composition including the flowable solid is compressed to provide sufficient surface contact between particles making up the flowable solid that the uncured composition will solidify into a stable solid composition. A sufficient quantity of particles (e.g. granules) in contact with one another provides binding of particles to one another effective for making a stable solid composition. Inclusion of a curing step may include allowing the pressed solid to solidify for a period of time, such as a few hours, or about 1 day (or longer). In additional aspects, the methods could include vibrating the flowable solid in the form or mold, such as the methods disclosed in U.S. Pat. No. 8,889,048, which is herein incorporated by reference in its entirety.

The use of pressed solids provide numerous benefits over conventional solid block or tablet compositions requiring high pressure in a tablet press, or casting requiring the melting of a composition consuming significant amounts of energy, and/or by extrusion requiring expensive equipment and advanced technical know-how. Pressed solids overcome such various limitations of other solid formulations for which there is a need for making solid cleaning compositions. Moreover, pressed solid compositions retain its shape under conditions in which the composition may be stored or handled.

By the term "solid", it is meant that the hardened composition will not flow and will substantially retain its shape under moderate stress or pressure or mere gravity. A solid may be in various forms such as a powder, a flake, a granule, a pellet, a tablet, a lozenge, a puck, a briquette, a brick, a solid block, a unit dose, or another solid form known to those of skill in the art. The degree of hardness of the solid cast composition and/or a pressed solid composition may range from that of a fused solid product which is relatively dense and hard, for example, like concrete, to a consistency characterized as being a hardened paste. In addition, the term "solid" refers to the state of the composition under the expected conditions of storage and use of the solid detergent composition. In general, it is expected that the detergent composition will remain in solid form when exposed to temperatures of up to approximately 100° F. and particularly up to approximately 120° F.

The resulting solid composition may take forms including, but not limited to: a cast solid product; an extruded, molded or formed solid pellet, block, tablet, powder, granule, flake; pressed solid; or the formed solid can thereafter be ground or formed into a powder, granule, or flake. In an exemplary embodiment, extruded pellet materials formed by the solidification matrix have a weight of between approximately 50 grams and approximately 250 grams, extruded solids formed by the composition have a weight of approximately 100 grams or greater, and solid block detergents formed by the composition have a mass of between approximately 1 and approximately 10 kilograms. The solid compositions provide for a stabilized source of functional materials. In some embodiments, the solid composition may be dissolved, for example, in an aqueous or other medium, to create a concentrated and/or use solution. The solution may be directed to a storage reservoir for later use and/or dilution, or may be applied directly to a point of use.

The following patents disclose various combinations of solidification, binding and/or hardening agents that can be utilized in the solid cleaning compositions of the present invention. The following U.S. patents are incorporated herein by reference: U.S. Pat. Nos. 7,153,820; 7,094,746; 7,087,569; 7,037,886; 6,831,054; 6,730,653; 6,660,707; 6,653,266; 6,583,094; 6,410,495; 6,258,765; 6,177,392; 6,156,715; 5,858,299; 5,316,688; 5,234,615; 5,198,198; 5,078,301; 4,595,520; 4,680,134; RE32,763; and RE32818.

Methods of Use

The solid triamine compositions may be incorporated into a variety of cleaning compositions, including for example floor cleaning composition, hard surface composition, or clean-in-place composition (i.e., for cleaning food and beverage or pharmaceutical equipment), detergent compositions and the like. The system is especially useful in the foodservice business on food soils. When a lipase is included in the system, the system and compositions are useful in removing fats and oils off of hard and soft surfaces in a kitchen.

Fats and oils in a kitchen build up over time, eventually forming a hard coating on surfaces. Floor tiles and back splashes near cooking surfaces eventually develop a sheen to them because of the hardened layers of fat and oil. Grout becomes discolored as fat and oil soils become embedded into the grout. Bar rags and mop heads accumulate fat and oil soils over time. In addition to having soil buildup, the foodservice industry needs to prevent outbreaks of food illness like *E. coli* and *Salmonella*. The invention is especially useful in this industry because of its ability to remove food soils and its antimicrobial properties.

Exemplary floor cleaning compositions include compositions for use in manual (i.e., mop and bucket) applications or in an automatic floor cleaning machines such as those manufactures by Tennant, Clarke and others. When used in an automatic floor cleaning machine, the composition provides the additional benefit of maintaining the cleanliness of the inside of the machine through the action of the enzyme and preventing odor and bacterial growth in the machine because of the antimicrobial properties.

Foodservice industries often collect bar rags, towels, and mop heads in a bucket that includes a laundry pre-treatment composition. The compositions may be used as a pre-treatment composition in the foodservice industry. The compositions are advantageous here because they can begin to break down food soils before the laundry even goes into the laundry machine.

The solid composition of the present invention comprises the active ingredients in a high concentration. The concentration of the active ingredients is calculated on the total weight of the solid composition of the present invention, if not otherwise stated. Before use, the solid composition of the present invention needs to be dissolved in an aqueous solution, preferably water, to obtain a ready-to-use solution. Preferably, the solid composition can be dissolved at the time of application and/or stored in a dilution device.

In some aspects the solid triamine compositions for use in generating a ready-to-use solution may have a ratio of the diacid to the biocidal triamine from about 1:10 to about 1:5, preferably from about 1:5 to about 1:4, and most preferably from about 1:2 to about 1:3. In addition, without being limited according to the invention, all ranges for the ratios recited are inclusive of the numbers defining the range.

Accordingly use of the solid triamine compositions may include concentrate compositions or may be diluted to form use compositions. In general, a concentrate refers to a composition that is intended to be diluted with water to provide a use solution that contacts an object to provide the desired cleaning, rinsing, or the like. The triamine composition that contacts the articles or surfaces to be washed, sanitized, disinfected or the like can be referred to as a concentrate or a use composition (or use solution) dependent upon the formulation employed in methods according to the invention. It should be understood that the concentration of the biocidal triamine, diacid and additional functional ingredients in the composition will vary depending on whether the composition is employed as a concentrate or as a use solution.

A use solution may be prepared from the concentrate by diluting the concentrate with water at a dilution ratio that provides a use solution having desired detersive properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to be removed and the like. In an embodiment, the concentrate is diluted at a ratio of between about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:250 and about 1:2,000 concentrate to water, and preferably between about 1:500 and about 1:750.

In an aspect of the invention, a use solution of the biocidal triamine composition provides between about 1 ppm to about 1000 ppm triamine, and between about 1 ppm to about 500 ppm diacid. In a preferred aspect of the invention, a use solution of the biocidal triamine composition has between about 1 ppm to about 500 ppm triamine, and between about 1 ppm to about 250 ppm diacid. In a still further aspect, a use solution of the biocidal triamine composition has between about 1 ppm to about 300 ppm triamine, and between about 1 ppm to about 250 ppm diacid. The ranges disclosed herein are not limited according to the invention, all ranges recited are inclusive of the numbers defining the range and include each integer within the defined range.

According to the invention, the solid composition can be dissolved in service water, deionized water or such at a sufficient proportion to obtain the concentrated solution and/or diluted ready-to-use solution set forth above.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Methods for producing pressed solid compositions for commercial sanitizing compositions employing biocidal triamines and enzymes were evaluated. Desired solidified compositions required performance efficacy that meets or preferably exceeds the commercially-available liquid product performance, as measured by cleaning performance and micro efficacy (i.e. sanitizing capability), along with other measurable including for example, odor reduction. Exemplary formulations evaluated for replacement solid compositions are set forth in Table 3.

TABLE 3

| Description | Liquid Sanitizing Composition (wt-%) | Liquid Composition (wt-%) |
|---|---|---|
| Water DI | 70-85 | 50-65 |
| Triamine (Lonzabac 12.100) | 2-4 | 0 |
| Acidulants | 5-10 | 5-10 |
| Lipase enzyme | 1-5 | 1-5 |
| Additional Functional Ingredients | 15-45 | 35-50 |
| Total | 100 | 100 |

For the evaluated formulations the additional functional ingredients included Alcohol Linear C12-16 ethoxylate, Polyether Siloxanes 5843 DRM, Amine oxide surfactant, and Monoethanolamine 99% IBC included in both compositions.

Solidification evaluations first evaluated neutralization of the biocidal triamine from an alkaline pH in the liquid formulation prior to solidification due to the liquid formulations requiring neutralization of the biocidal triamine from the alkaline pH of about 10-11 to a pH of about 8.5 for stabilization of the lipase enzyme formulated therein. The neutralization of the biocidal triamine minimizes enzyme degradation within the composition, while maximizing enzyme stability. The biocidal triamine Lonzabac 12.100 available from Lonza Inc. was evaluated for solid compositions as the triamine is commercially-available in liquid formulations as shown in Table 2.

As shown in Table 4, various acids were combined in varying concentrations with the biocidal triamine Lonzabac 12.100 to assess the stabilization of the neutralized compositions for use in a solid composition. The desired amounts of triamine were weighed out and combined with the desired amounts of the evaluated solid acids. The triamine and acids were gently mixed to disperse the acid in the triamine. The solutions were left undisturbed for approximately 1.5-2.5 hours and observations on the form of the triamine/acid mixture were made. If the mixture had expanded into a powder it was gently mixed to separate particles. For each evaluation a 1% solution of each powder was made to determine solubility and pH.

TABLE 4

| ID | Acid | Amine | MW | % Acid (wt-%) | % amine (wt-%) | Acid:amine (molar) | Observations | Water solubility | pH of 1% |
|---|---|---|---|---|---|---|---|---|---|
| 1 | Citric | Lonzabac 12.100 | 192 | 25 | 75 | 0.519097222 | Free flowing powder | Cloudy/ppt/ gel ball | N/A |
| 2 | Tartaric | Lonzabac 12.100 | 150 | 18.2 | 81.2 | 0.446781609 | Free flowing powder | Clear solution | 9.26 |
| 3 | Tartaric | Lonzabac 12.100 | 150 | 25 | 75 | 0.664444444 | Free flowing powder | Clear solution | 8.85 |
| 4 | Tartaric | Lonzabac 12.100 | 150 | 30.7 | 69.3 | 0.883049543 | Free flowing powder | Clear solution | 8.29 |
| 5 | Tartaric | Lonzabac 12.100 | 150 | 35.7 | 64.3 | 1.106718507 | Free flowing powder | Clear solution | 7.48 |
| 6 | Benzoic | Lonzabac 12.100 | 122 | 25 | 75 | 0.816939891 | Waxy solid | Clear solution | 8.76 |
| 7 | Mandelic | Lonzabac 12.100 | 152 | 25 | 75 | 0.655701754 | Very hard solid | Cloudy white soln | 8.05 |
| 8 | Sulfamic | Lonzabac 12.100 | 97 | 25 | 75 | 1.027491409 | very hard solid | Clear solution | 8.33 |
| 9 | Boric | Lonzabac 12.100 | 62 | 25 | 75 | 1.607526882 | Clear gel base w/pwdr top | Clear solution | 8.18 |
| 10 | Malic | Lonzabac 12.100 | 134 | 25 | 75 | 0.743781095 | Free flowing powder | Clear solution | 7.87 |
| 11 | Malonic | Lonzabac 12.100 | 104 | 25 | 75 | 0.958333333 | Hard solid | Clear solution | 7.38 |
| 12 | Maleic | Lonzabac 12.100 | 116 | 25 | 75 | 0.859195402 | hard solid, broke into pwdr | Clear solution | 7.89 |
| 13 | Succinic | Lonzabac 12.100 | 118 | 25 | 75 | 0.844632768 | Very hard solid | Clear solution | 8.04 |
| 14 | Adipic | Lonzabac 12.100 | 146 | 25 | 75 | 0.682648402 | Very hard solid | Clear solution | 8.16 |
| 15 | Aspartic | Lonzabac 12.100 | 133 | 25 | 75 | 0.749373434 | Very thick paste, grainy | | |
| 16 | EDTA Acid | Lonzabac 12.100 | 292 | 36 | 64 | 0.575984589 | damp powder | Clear w/some EDTA ppt | 8.41 |

TABLE 4-continued

| ID | Acid | Amine | MW | % Acid (wt-%) | % amine (wt-%) | Acid:amine (molar) | Observations | Water solubility | pH of 1% |
|---|---|---|---|---|---|---|---|---|---|
| 17 | IDA | Lonzabac 12.100 | 133 | 25 | 75 | 0.749373434 | dry powder, did not swell | clear | 8.95 |
| 18 | glycine | Lonzabac 12.100 | 75 | 25 | 75 | 1.328888889 | wet powder | Cloudy | N/A |
| 19 | glycine | Lonzabac 12.100 | 75 | 50 | 50 | 3.986666667 | dry powder | Cloudy | N/A |
| 20 | lysine | Lonzabac 12.100 | 146 | 25 | 75 | 0.682648402 | dry powder | Cloudy | N/A |
| 21 | lysine | Lonzabac 12.100 | 146 | 50 | 50 | 2.047945205 | dry powder | Cloudy | N/A |
| 22 | gluconic | Lonzabac 12.100 | 196 | 25 | 75 | 0.508503401 | waxy solid | Clear | 8.94 |
| 23 | gluconic | Lonzabac 12.100 | 196 | 50 | 50 | 1.525510204 | hard waxy solid | Clear | 8.41 |
| 24 | glutamic | Lonzabac 12.100 | 147 | 25 | 75 | 0.678004535 | dry powder | Clear | 8.48 |
| 25 | glutamic | Lonzabac 12.100 | 147 | 50 | 50 | 2.034013605 | hard brittle solid | Clear | 8.1 |
| 26 | dipicolinic | Lonzabac 12.100 | 167 | 25 | 75 | 0.596806387 | dry powder | Hazy | 8.94 |
| 27 | dipicolinic | Lonzabac 12.100 | 167 | 50 | 50 | 1.790419162 | very hard solid | ppt on bottom | 4.71 |
| 28 | octanoic | Lonzabac 12.100 | 144 | 25 | 75 | 0.69212963 | opaque cream | Clear | 9.61 |
| 29 | octanoic | Lonzabac 12.100 | 144 | 50 | 50 | 2.076388889 | orange waxy solid | Clear | 7.59 |
| 30 | decanoic acid | Lonzabac 12.100 | 172 | 25 | 75 | 0.579457364 | opaque cream | Cloudy/ppt/ gel ball | N/A |
| 31 | decanoic acid | Lonzabac 12.100 | 172 | 50 | 50 | 1.738372093 | orange waxy solid | Clear solution | 9.26 |

As set forth in Table 3, the step of neutralizing the alkaline biocidal triamine with a solid acid unexpectedly resulted in a number of solid triamine compositions. Free flowing powders, hard solids and very hard solids were unexpectedly obtained from the reaction of the triamine with the solid acids. The pastes generated were not sufficiently solidified to proceed for additional evaluation. In an aspect of the invention, combinations of triamines with a solid acid resulting in a composition having a water content of 10 wt-% or greater of water are undesirable formulations. As a further unexpected benefit the solid biocidal triamines allowed formulation containing predominately active triamine. In an aspect, at least about 90 wt-% active biocidal triamine can be formulated into the solid compositions. According to the invention the formulations are suitable for use in various solids, namely pressed solids. In other aspects, the solids may include cast solids, extruded solids, and the like.

Example 2

Following the testing of Example 1 looking at the neutralization of the biocidal triamine with a solid acid, additional solid acids were evaluated at the 25:75 ratio/% acid to triamine, the results of which are shown in Table 5.

TABLE 5

| Acid | Acid MW | MP | % Acid (wt-%) | % Amine (wt-%) | molar ratio | Water Solubility | pH of 1% | Observations |
|---|---|---|---|---|---|---|---|---|
| Formic | 46.03 | 47.1 | 25 | 75 | 2.16525454 | N/A | N/A | Gel ball formed; vigerous reaction; discoloration |
| Acetic | 60.05 | 61 | 25 | 75 | 1.659728 | Yes | 8.31 | Very hard solid formed |
| Acrylic | 72.06 | 57 | 25 | 75 | 1.38310667 | No | N/A | Hard gel formed; not flowable but malleable |
| Sorbic | 112 | 275 | 25 | 75 | 0.88988095 | Yes | 9.26 | Waxy soft solid formed |
| Fumaric | 116.07 | 548 | 25 | 75 | 0.85867724 | Yes | 8.65 | Solidified into paste consistency |
| maleic | 116.07 | 275 | 25 | 75 | 0.85867724 | Yes | 7.89 | Hard solid formed; broke into powder |
| Caproic (hexanoic) | 116.16 | 25.9 | 25 | 75 | 0.85801194 | Yes | 9.21 | Did not solidify; homogenous liquid |
| Succinic | 118.09 | 363 | 25 | 75 | 0.84398905 | Yes | 8.04 | Very hard solid formed |
| Benzoic | 122 | 252 | 25 | 75 | 0.81693989 | Yes | 8.76 | Hard solid formed |
| Oxalic (ethanedioic) | 126.07 | 216 | 25 | 75 | 0.79056609 | No | N/A | Very hard solid formed; rapid solidification; discoloration |
| Malic | 134 | 266 | 25 | 75 | 0.74378109 | Yes | 7.87 | Free flowing powder formed |
| Salicylic | 138 | 317 | 25 | 75 | 0.72222222 | N/A | N/A | Did not react; powder on bottom, liquid on top |
| Tartaric | 150 | 170 | 25 | 75 | 0.66444444 | Yes | 9.26 | Free flowing powder formed |
| mandelic | 152 | 246 | 25 | 75 | 0.65570175 | No | 8.05 | Very hard solid formed |

TABLE 5-continued

| Acid | Acid MW | MP | % Acid (wt-%) | % Amine (wt-%) | molar ratio | Water Solubility | pH of 1% | Observations |
|---|---|---|---|---|---|---|---|---|
| Citric | 192 | 313 | 25 | 75 | 0.51909722 | No | N/A | Free flowing powder formed |
| Gluconic | 196 | 268 | 25 | 75 | 0.5085034 | Yes | 8.41 | Waxy solid formed |

Example 3

Additional formulations of the biocidal triamine and solid acid were further evaluated to assess melting points and percent water content in the formulated pressed solid compositions. Exemplary formulations are shown in Table 6 were formulated into pressed solids after following the experimentation set forth in Example 1.

TABLE 6

| Contents (wt-%) | Melting point (° C.) | Water Content (wt-%) |
|---|---|---|
| 81.8% lonzabac + 18.2% Tartaric acid | 57.57 | 0.6 |
| 75% lonzabac + 25% Tartaric acid | 55.38 | 0.6 |
| 69.3% lonzabac + 30.7% Tartaric acid | 75.5 | 0.5 |
| 64.3% lonzabac + 35.7% Tartaric acid | 73.11 | 0.6 |
| 75% lonzabac + 25% Malic acid | 85.55 | 0.5 |
| 22.5% lonzabac + 7.5% Tartaric + 35% 4Na-EDTA + 35% Na Sulfate | 51.15 | 4.2 |
| 64.3% Lonzabac + 35.7% Acid EDTA | 113.95 | 0.7 |
| 75% Lonzabac + 25% Aspartic acid | 76.25 | 0.5 |
| 75% lonzabac + 25% Citric acid | 87.91 | 0.6 |

The results shown in Table 6 reflect a preferred pressed solid composition having a water content of less than 1 wt-%.

Example 4

Various formulations of the biocidal triamine and solid acid were further evaluated for formulation into pressed solid compositions. The exemplary formulations are shown in Table 7 were formulated into pressed solids after following the experimentation set forth in Example 1.

TABLE 7

| Description | Tablet 1 (wt-%) | Tablet 2 (wt-%) | Tablet 3 (wt-%) | Tablet 4 (wt-%) |
|---|---|---|---|---|
| Lonzabac 12.100 | 75 | 64.3 | 22.5 | 22.5 |
| Tartaric acid | 25 | 35.7 | 7.5 | 7.5 |
| Tetrasodium EDTA | 0 | 0 | 35 | 35 |
| Sodium Sulfate anhydrous | 0 | 0 | 35 | 35 |
| Total | 100 | 100 | 100 | 100 |

50 grams of each of the 3 tablet formulations were weighted to be pressed. Then a 50 gram sample was placed into a small 1.5" diameter stainless steel dye and pressed using a carver press at 2000 psi for 20 seconds. The tablet was then removed from the dye. The results indicated that the pressed tablets were hard and retained their shape upon being ejected from the mold.

The inventions being thus described, it will be obvious that the same may be varied in many ways. Such variations are not to be regarded as a departure from the spirit and scope of the inventions and all such modifications are intended to be included within the scope of the following claims.

The above specification provides a description of the manufacture and use of the disclosed compositions and methods. Since many embodiments can be made without departing from the spirit and scope of the invention, the invention resides in the claims.

What is claimed is:

1. A solid triamine composition formed by a process comprising:
   providing a composition comprising a triamine comprising any one of the following formulas:

R—NH—[(CH$_2$)$_r$NH]$_y$—(CH$_2$)$_m$—NH$_2$

wherein:
   R is a linear or branched alkyl residue with 1 to 22 carbon atoms,
   m, r, and y independently represent an integer ranging from 1 to 6;
   a solid diacid comprising adipic acid, aspartic acid, dipicolinic acid, malic acid, malonic acid, oxalic acid, succinic acid, or tartaric acid or combinations thereof; and
   two or more of an amine oxide surfactant, a functional siloxane surfactant or an enzyme, wherein the ratio of the diacid to the triamine is from about 1:10 to about 1:1;
   combining the triamine, the solid diacid, and the two or more of the amine oxide surfactant, the functional siloxane surfactant or the enzyme; and
   at least partially neutralizing the triamine and the solid diacid to form a solid matrix;
   wherein the composition is formed at a temperature of between about 21° C. and about 55° C. without casting or extrusion.

2. The composition of claim 1, further comprising a hardening agent.

3. The composition of claim 1, wherein the enzyme is a lipase.

4. The composition of claim 1, further comprising at least one functional ingredient selected from the group consisting of: additional surfactants that are not amine oxide surfactant or functional siloxane surfactant, chelating agents, sequestering agents, detergents, alkaline sources, builders, rinse aids, hardening agents, bleaching agents, sanitizers, activators, builders, fillers, defoaming agents, anti-redeposition agents, optical brighteners, dyes, odorants, stabilizing agents, dispersants, additional enzymes, corrosion inhibitors, thickeners and solubility modifiers.

5. The composition of claim 1, further comprising one or more additional functional siloxane surfactant(s).

6. The composition of claim 1, comprising up to about 99 wt-% of the triamine and between about 1 wt-% to about 50 wt-% of the solid diacid.

7. The composition of claim 1, comprising between about 10 wt-% to about 70 wt-% of the triamine, and between about 2.5 wt-% to about 40 wt-% of the solid diacid.

8. The composition of claim 1, further comprising between about 1 wt-% to about 40 wt-% of a chelant.

9. A kit comprising:
the solid triamine composition of claim 1; and
instructions for dilution and use.

10. A method of making a solid triamine composition comprising:
combining the triamine and solid diacid of claim 1; and
reacting the triamine with the solid diacid to form an at least partially neutralized solid matrix;
wherein the ratio of the diacid to the triamine is from about 1:10 to about 1:1; and
wherein the composition is formed at a temperature of between about 21° C. and about 55° C. and remains solid below about 50° C. without casting or extrusion.

11. The method of claim 10, wherein the solid is a pressed solid.

12. The method of claim 11, wherein the pressed solid has a water content of less than about 10 wt-%.

13. The method of claim 10, wherein after reacting the triamine and the solid diacid to form the solid, the solid is further cast or extruded.

14. The method of claim 10, further comprising combining a hardening agent with the triamine and the solid diacid.

15. The method of claim 14, wherein the enzyme is a lipase.

16. A method of cleaning, sanitizing or disinfecting comprising:
providing the solid triamine composition of claim 1;
dissolving the solid triamine composition in an aqueous solution to generate a use solution comprising between about 1 ppm to about 1000 ppm of the triamine and between about 1 ppm to about 500 ppm of the solid diacid; and
contacting an article or surface with the use solution for cleaning, sanitizing, and/or disinfecting.

17. The method of claim 16, wherein the cleaning, sanitizing, or disinfecting is a rinse step or a lubricating step.

18. The method of claim 16, wherein the use solution of the solid triamine compositions provides between about 1 ppm to about 500 ppm triamine, and between about 1 ppm to about 250 ppm solid diacid.

19. The method of claim 16, wherein the surface is a hard surface.

20. The method of claim 19, wherein the hard surface is a counter top, tile, floor, wall, panel, window, plumbing fixture, kitchen furniture, bathroom furniture, appliance, engine, circuit board and/or dish ware.

* * * * *